United States Patent [19]

Wolf

[11] 3,969,525

[45] July 13, 1976

[54] METHOD FOR REDUCING THE HEART BEAT FREQUENCY

[75] Inventor: Martin Wolf, Geisenheim, Johannisberg, Germany

[73] Assignee: Boehringer Ingelheim GmbH, Ingelheim am Rhein, Germany

[22] Filed: Jan. 16, 1975

[21] Appl. No.: 541,381

[30] Foreign Application Priority Data

Feb. 1, 1974   Germany.......................... 24047549

[52] U.S. Cl. ............................................... 424/273
[51] Int. Cl.$^2$...................................... A61K 31/415
[58] Field of Search ................................... 424/273

[56] References Cited
UNITED STATES PATENTS 3,202,660   8/1965   Zeile et al............................. 260/254

OTHER PUBLICATIONS

Boehringer, -Chem. Abst. vol. 64 (1966) p. 2096e.

*Primary Examiner*—Sam Rosen
*Attorney, Agent, or Firm*—Hammond & Littell

[57] ABSTRACT

Pharmaceutical dosage unit compositions for the treatment of tachycardia and angina pectoris, which contain 2-(2',6'-diethylphenyl-amino)-1,3-diazacyclopentene-(2) or a non-toxic, pharmaceutically acceptable acid addition salt thereof as an active ingredient; and a method of slowing the heart rate therewith.

1 Claim, No Drawings

METHOD FOR REDUCING THE HEART BEAT FREQUENCY

This invention relates to novel pharmaceutical dosage unit compositions for the treatment of tachycardia and angina pectoris in humans.

More particularly, the present invention relates to a novel method of treating acute attacks of tachycardia and angina pectoris in humans by enterally or parenterally administering to the patient an effective amount of 2-(2', 6'-diethylphenyl-amino)-1,3-diazacyclopentene-(2) or a non-toxic acid addition salt thereof, as well as to pharmaceutical dosage unit compositions containing said compound or said acid addition salt as an active ingredient.

THE PRIOR ART 2-(2',6'-Diethylphenyl-amino)-1,3-diazacyclopentene-(2) and non-toxic, pharmaceutically acceptable acid addition salts thereof are disclosed in U.S. Pat. No. 3,202,660, issued Aug. 24, 1965. That patent further discloses that the compounds in question exhibit highly effective vasoconstrictor activities and, for therapeutic purposes, are preferably applied as active ingredients in compositions adapted for topical application to mucous membrane areas requiring vasoconstrictor therapy, especially nose drops, nasal sprays and ointments.

Furthermore, U.S. Pat. No. 3,190,802, issued June 22, 1965, discloses the use of 2-(2',6'-diethylphenyl-amino)-1,3-diazacyclopentene-(2) and its non-toxic acid addition salts as piloerector ingredients in topical shaving compositions, such as pre-shave lotions and shaving creams.

The enteral or parenteral administration of structurally related 2-phenylamino-1,3-diazacyclopentenes-(2) and their non-toxic acid addition salts is disclosed in U.S. Pat. Nos. 3,236,857, 3,454,701 and 3,666,861, but none of these prior patents suggests that these related compounds could be used for slowing the heart rate.

THE INVENTION

I have now discovered that when 2-(2',6'-diethylphenyl-amino)-1,3-diazacyclopentene-(2) or a non-toxic, pharmaceutically acceptable acid addition salt thereof is enterally or parenterally administered to a human patient, a slowing of the heart rate is effected.

This surprising and heretofore unknown pharmacological activity of the known compounds above referred to was ascertained in a clinical study in which 10 normal, healthy human volunteers participated. The test subject group consisted of eight male and two female students whose age ranged from 22 to 32 years and who had a body weight between 62 and 84 kg.

The effects of three different perorally administered doses of 2-(2',6'-diethylphenyl-amino)-1,3-diazacyclopentene-(2), namely, 0.5, 1 and 2 mgm, upon the heart rate and the blood pressure of the test subjects, both at rest and while physically exercising, were investigated. Possible toxic side effects were monitored by frequent determinations of hemoglobin, sedimentation rate, leucocytes, thrombocytes, prothrombin, glutamine-pyruvate-transaminase, bilirubin and plasma creatinine, as well as protein and glucose in the urine. Prior to the test, as well as under the influence of the highest dose of the test compound, an electrocardiogram (EKG) with three standard electrodes and six precordial electrodes was prepared of each test subject.

The human volunteers were subjected to the test 2 hours after the last meal. The heart rate of the untreated test subjects was recorded by means of an EKG with one bipolar chest electrode and a cardiotachometer, first for 15 to 20 minutes in the sitting position and then for 15 minutes in the supine position; simultaneously, the blood pressure was recorded in the usual manner. The same parameters were then measured in the standing position, the heart rate being continuously recorded and the blood pressure every 5 minutes. The same parameters were subsequently again measured and recorded while the test subjects exercised on an electrically braked stationary bicycle, first for 5 minutes at a work rate of 450 kiloponds/minute and then for 5 minutes at a work rate of 750 kiloponds/minute. Thereafter, each test subject ingested a gelatin capsule containing 0.5 mgm of 2-(2',6'-diethylphenyl-amino)-1,3-diazacyclopentene-(2), and the heart rate and blood pressure were intermittently recorded over a period of 15 to 20 minutes while the test subjects were in the sitting position; the measurement of these parameters was subsequently repeated 90 minutes later.

The entire above-described procedure was repeated twice at intervals of 1 to 3 days with the same test subjects, except that the peroral dose of 2-(2',6'-diethylphenyl-amino)-1,3-diazacyclopentene-(2) was increased to 1 and 2 mgm, respectively.

This clinical study unequivocally showed that the enteral administration of 2-(2',6'-diethylphenyl-amino)-1,3-diazacyclopentene-(2) results in a significant, dose-dependent reduction of the heart rate at rest as well as under a work load. The heart rate at rest was reduced by 15 to 29%. The 0.5 mgm dose did not affect the heart rate under a work load, but a dose of 1 mgm reduced the heart rate under a work load by about 10%.

A dose of 2 mgm produced a drop of about 11% in the systolic blood pressure under a work load, which corresponds to a decrease in the systolic blood pressure of about 15 mm Hg. The blood pressure remained unchanged at rest.

The monitoring of the biochemical parameters showed no toxic effects upon the liver, the kidneys and the bone marrow.

The above clinical test results show that the enteral or parenteral administration of 0.5 to 5 mgm, preferably 2 mgm, of 2-(2',6'-diethylphenyl-amino)-1,3-diazacyclopentene-(2) or a non-toxic, pharmaceutically acceptable acid addition salt thereof is indicated for the treatment of acute tachycardia and angina pectoris in adult humans.

For pharmaceutical purposes, 2-(2',6'-diethylphenyl-amino)-1,3-diazacyclopentene-(2) or a non-toxic acid addition salt thereof is administered to adult humans perorally or parenterally as an active ingredient in customary dosage unit compositions, that is, ingestible or injectable compositions in dosage unit form consisting essentially of an inert pharmaceutical carrier and one effective dosage unit, i.e. 0.5 to 5 mgm, of the active ingredient, such as tablets, coated pills, capsules, wafers, powders, solutions, suspensions, emulsions, syrups, suppositories and the like.

The following examples illustrate a few pharmaceutical dosage unit compositions comprising 2-(2',6'-diethylphenyl-amino)-1,3-diazacyclopentene-(2) or a non-toxic acid addition salt thereof as an active ingredient and represent the best modes contemplated of putting the invention into practical use. The parts are parts by weight unless otherwise specified.

EXAMPLE 1

Tablets

The tablet composition is compounded from the following ingredients:

| | |
|---|---|
| 2-(2',6'-Diethylphenyl-amino)-1,3-diazacyclopentene-(2) | 2.0 parts |
| Lactose | 53.0 parts |
| Corn starch | 20.0 parts |
| Soluble starch | 4.0 parts |
| Magnesium stearate | 1.0 parts |
| Total | 80.0 parts |

Preparation:

The diazacyclopentene compound is intimately admixed with the lactose and the corn starch, the mixture is moistened with an aqueous 10% solution of the soluble starch, the moist mass is forced through a 1 mm-mesh screen, and the resulting granulate is dried at 40°C. and again passed through the screen. The dry granulate is admixed with the magnesium stearate, and the composition is compressed into 80 high-tablets in a conventional tablet making machine. Each tablet contains 2 mgm of the diazacyclopentene compound and is a safe and effective oral dosage unit composition for the treatment of acute tachycardia and angina pectoris in adult humans.

EXAMPLE 2

Coated Pills

The pill core composition is compounded from the following ingredients:

| | |
|---|---|
| 2-(2',6'-Diethylphenyl-amino)-1,3-diazacyclo-pentene-(2) | 2.0 parts |
| Corn starch | 23.0 parts |
| Sec. calcium phosphate | 65.0 parts |
| Magnesium stearate | 10.0 parts |
| Total | 100.0 parts |

Preparation

The diazacyclopentene compond is intimately admixed with the corn starch and the secondary calcium phosphate, and the mixture is moistened and granulated as in the preceding example. The dry granulate is admixed with the magnesium stearate, and the composition is compressed into 100 mgm-pill cores which are subsequently coated with a thin shell consisting essentially of a mixture of sugar, titanium dioxide, talcum and gum arabic, and finally polished with beeswax. Each coated pill contains 2 mgm of the diazacyclopentene compound and is a safe and effective oral dosage unit composition for the treatment of acute tachycardia and angina pectoris in adult humans.

EXAMPLE 3

Drop Solution

The solution is compounded from the following ingredients:

| | |
|---|---|
| 2-(2',6'-Diethylphenyl-amino)-1,3-diazacyclopentene hydrochloride | 0.2 parts |
| Methyl p-hydroxybenzoate | 0.07 parts |
| Propyl p-hydroxybenzoate | 0.03 parts |
| Demineralized water q.s.ad | 100.00 parts by vol. |

Preparation

The first three ingredients are dissolved in a sufficient amount of demineralized water, and the solution is diluted to the indicated volume with additional demineralized water. 1 ml of the solution (about 20 drops) contains 2 mgm of the diazacyclopentene compound and is a safe and effective oral dosage unit composition for the treatment of acute tachycardia and angina pectoris in adult humans.

EXAMPLE 4

Hypodermic Solution

The solution is compounded from the following ingredients:

| | |
|---|---|
| 2-(2',6'-Diethylphenyl-amino)-1,3-diazacyclopentene-(2) | 4 parts |
| Sodium chloride | 18 parts |
| Distilled water q.s.ad | 2000 parts by vol. |

Preparation

The diazacyclopentene compound and the sodium chloride are dissolved in a sufficient amount of distilled water, the solution is diluted with additional distilled water to the indicated volume and then filtered until free from suspended matter, and the filtrate is filled into 1 cc-ampules which are subsequently sealed and sterilized. Each ampule contains 2 mgm of the diazacyclopentene compound, and its contents are a safe and effective injectable dosage unit composition for the treatment of acute tachycardia and angina pectoris in adult humans.

EXAMPLE 5

Powder

The powder is compounded from the following ingredients:

| | |
|---|---|
| 2-(2',6'-Diethylphenyl-amino)-1,3-diazacyclopentene-(2) hydrochloride | 2.5 parts |
| Lactose | 997.5 parts |
| Total | 1000.0 parts |

Preparation

The diazacyclopentene compound is intimately admixed with a portion of the lactose and, while continuing to stir the mixture intensively, the remaining amount of lactose is slowly added. 1.0 gm of the resulting powder contains 2.5 mgm of the diazacyclopentene compound and is a safe and effective oral dosage unit composition for the treatment of acute tachycardia and angina pectoris in adult humans.

EXAMPLE 6

Granulate

The granulate is compounded from the following ingredients:

| | |
|---|---|
| 2-(2',6'-Diethylphenyl-amino)-1,3-diazacyclopentene-(2) nitrate | 2.0 parts |

| | |
|---|---|
| Lactose | 498.0 parts |
| Total | 500.0 parts |

Preparation

The ingredients are intimately admixed with each other, as described in the preceding example, the mixture is uniformly moistened with distilled water, the moist mass is forced through a 1.5 mm-mesh screen, and the resulting granulate is dried. 0.5 gm of the dry granulate contains 2 mgm of the diazacyclopentene compound and is a safe and effective oral dosage unit composition for the treatment of acute tachycardia and angina pectoris in adult humans.

The amount of active ingredient in the above illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. The method of slowing the heart rate in an adult human in need of such treatment, which comprises enterally or parenterally administering to said adult human 0.5 to 5 mgm of 2-(2',6'-diethylphenyl-amino)-1,3-diazacyclopentene-(2) or a non-toxic, pharmaceutically acceptable acid addition salt thereof.

* * * * *